United States Patent [19]

Gericke

[11] Patent Number: 5,069,666
[45] Date of Patent: Dec. 3, 1991

[54] INTRAVENOUS ADMIXTURE PROTECTIVE DEVICE

[75] Inventor: Stephen H. Gericke, Oklahoma City, Okla.

[73] Assignee: Safe Medical Devices Inc., Oklahoma City, Okla.

[21] Appl. No.: 652,990

[22] Filed: Feb. 8, 1991

[51] Int. Cl.⁵ .................. A61M 37/00; A61M 5/00
[52] U.S. Cl. .................... 604/86; 604/263; 604/283
[58] Field of Search ............... 604/167, 171, 192, 162, 604/201, 263, 283, 284, 82, 83, 85, 86, 87, 88, 905; 128/912, 919; 604/280

[56] References Cited

U.S. PATENT DOCUMENTS

| | | |
|---|---|---|
| 4,573,975 | 3/1986 | Frist et al. . |
| 4,629,455 | 12/1986 | Kanno ................................ 604/283 |
| 4,740,204 | 4/1988 | Masters et al. . |
| 4,767,412 | 8/1988 | Hymanson . |
| 4,799,927 | 1/1989 | Davis et al. . |
| 4,840,618 | 6/1989 | Marvel . |
| 4,943,283 | 7/1990 | Hogan ................................ 604/263 |
| 4,966,582 | 10/1990 | Sit et al. ................................ 604/86 |
| 4,986,817 | 1/1991 | Code ................................ 604/263 |
| 5,000,742 | 3/1991 | Morrison ............................ 604/263 |

Primary Examiner—C. Fred Rosenbaum
Assistant Examiner—Sharon Finkel

[57] ABSTRACT

A conical shield for attachment to a conventional admixture site which effectively and economically provides: 1) positive needle-thick protection for an individual administering medication; 2) secure locking of the device to the admixture site; 3) security from accidental disconnection of the intravenous solution and; 4) a method whereby the caps of hypodermic needles may be safely removed, stored during injection of medication or withdrawal of body fluids and returned to cover the needle following use.

14 Claims, 1 Drawing Sheet

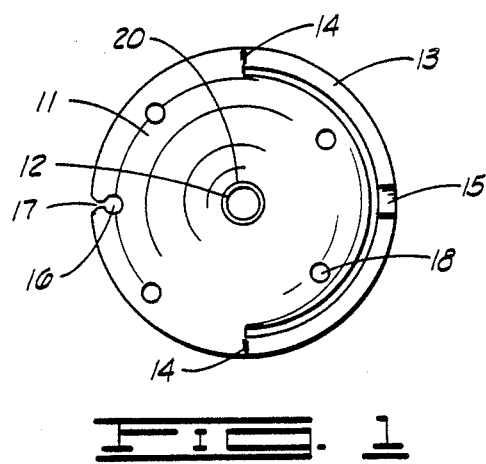
FIG. 1
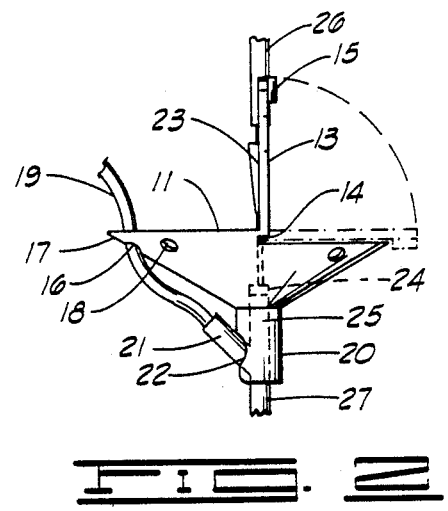
FIG. 2
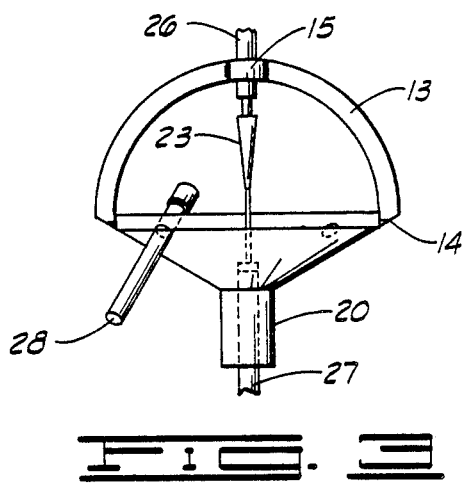
FIG. 3
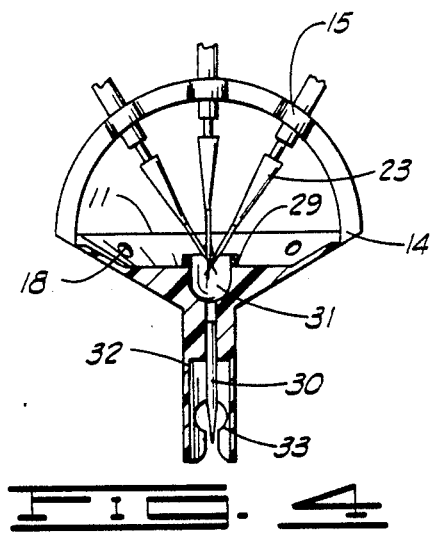
FIG. 4
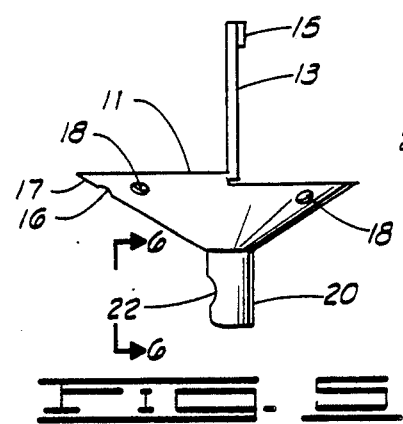
FIG. 5
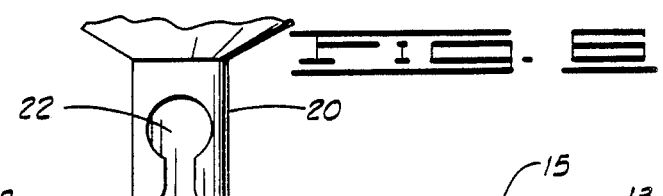
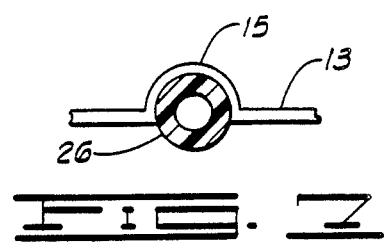
FIG. 7

INTRAVENOUS ADMIXTURE PROTECTIVE DEVICE

BACKGROUND OF THE INVENTION

It is well known, especially in the medical and health-care communities, that incurable and potentially fatal diseases may be transmitted from infected persons to health-care personnel by inadvertent or accidental puncture of the skin of attending technicians during routine extraction of body fluids for laboratory analysis and diagnosis or during the administration of therapeutic drugs intravenously or intramuscularly by hypodermic means. Many of these punctures occur when the hypodermic needle is being returned to a protective sheath following extraction or injection in a process generally referred to as "re-capping the needle". The high, and increasing incidence of disease transmittable in this manner, such as human immunodeficiency virus (HIV), acquired immune deficiency syndrome (AIDS) and the hepatic diseases such as Hepatitis-B and Hepatitis-non A and non B have raised grave concerns in the medical community, to the extent that some health-care professionals are leaving the field for fear of contracting a dread or presently incurable disease.

Since the discovery of these highly communicable diseases and the manner in which they may be transmitted from one individual to another many devices have been developed to reduce the risk and incidence of accidental "needle sticks". Among these developments is a protective shield for a needle receiver, the subject of U.S. Pat. No. 4,573,975 granted to Frist et al., wherein a collapsible disc surrounding the opening in the needle cap is disclosed. Said collapsible disc opens in response to the removal of the needle from the cap and provides a shield to prevent the user from being stuck by the needle in the event that entry of the needle into the sheath is not achieved while recapping the needle after use.

In other examples of the prior art, Masters et al., in U.S. Pat. No. 4,740,204 disclose a needle cap of a more nearly standard configuration equipped with a flared funnel-like shield surrounding the entry to the needle cap to guide errant needles into the opening in the cap and further provides a second shield of disc of funnel shape to remove the users fingers from the area proximate the target site. Similarly, Hymanson in U.S. Pat. No. 4,767,412 employs a funnel-shaped guard provided with a gripping means to retain the needle cap and to accommodate a plurality of sizes of said caps. Again similarly, in U.S. Pat. No. 4,799,927 Davis et al. disclose yet another funnel-like device to channel the used needle into the protective cap. Finally, Marvel in U.S. Pat. No. 4,840,618 discloses a Medical Safety Device which provides a shield with an elevated peripheral rim to protect the fisted hand of a person holding a test tube.

While all these examples of the prior art provide some manner of protection and benefit to the user, none have addressed the most critical issue and the principal reason that needle strikes occur; the proximity of the hand to the target area when re-capping a used hypodermic needle.

It is the object of the present invention to provide an intravenous admixture protective device with a means for preventing needle strikes when inserting and removing admixture needles, having means to securely attach said protective device to the admixture site, to the primary intravenous tubing and comprising means for preventing accidental disconnection of intravenous admixture tubing while providing a safe location for the storage of needle caps and a safe method for re-capping used hypodermic needles.

SUMMARY OF THE INVENTION

The present invention is a device for attachment to a conventional intravenous admixture site which provides needle stick protection for an individual administering intravenous medication; positive locking attachment to the admixture site; security from accidental disconnect of one or a plurality of admixture needles; and also provides a location for the storage of needle caps used in admixture and other intravenous injection procedures and a method whereby said needles may be safely re-capped following their use.

BRIEF DESCRIPTION OF THE DRAWING FIGURES

FIG. 1 is an overall plan view of the device viewed from overhead prior to installation on the admixture site.

FIG. 2 is an elevational view of the device installed on the admixture site with an admixture needle inserted and locked into place so as to administer a secondary medication.

FIG. 3 is an elevational view of the device as in FIG. 2, rotated 90° clockwise.

FIG. 4 is an alternate embodiment of the device which provides a larger admixture site to accommodate a plurality of needles and a self-contained needle for insertion into the conventional admixture site in partial cut-away view.

FIG. 5 is an elevational view of the device prior to attachment to the conventional admixture site showing the slotted hole lock which secures the device in place for use.

FIG. 6 depicts the slotted hole lock shown in FIG. 5 rotated 90° counter-clockwise and viewed at 6—6.

FIG. 7 depicts in plan view, detail of the semi-detached segment and cylindrical depression of 190° securely retaining intravenous tubing.

DETAILED DESCRIPTION OF THE DRAWING FIGURES

The embodiment of the present invention is depicted in FIGS. 1, 2 and 3 of the drawings wherein a truncated conical shield 11 joins a central cylinder 20 at the frustum of the cone. Said cylinder 20 having an opening 12 which is internally sized to closely accommodate the injection port of a conventional admixture site 25, said conical shield 11 and cylinder 20 being of unitary construction of a plastic compound such as polyethylene, having properties to render it highly resistant to puncture by hypodermic needles and of a sufficient thickness to provide adequate strength to perform the several functions which are the object of the present invention. Said conical shield 11 has about a portion of its periphery, a semi-detached segment 13, said segment being attached by hinge-points 14, said hinge-points being situate in diametric opposition to allow the segment 13 to be raised into perpendicularity to the base of the conical shield 11 in the manner of a "bail" or handle of a water pail. Said segment 13 has at its mid-point, a cylindrical depression 15 the inner diameter of which is equal to the outside diameter of conventional intravenous tubing, including an angle of 190° to be capable of securely retaining intravenous tubing, proximate the periphery thereof, said hole being provided with a slotted opening 17 extending radially outward to the peripheral rim of the conical shield 11 said slotted opening having its exterior corners relieved and rounded to facilitate the entry of intravenous tubing to said hole 16. The conical shield 11 also comprises a plurality of holes 18 proximate the periphery thereof, said holes being sized to accommodate conventional hypodermic needle sheaths or "caps". Further clarification of the function of the present invention is obtainable from the depiction in FIG. 2 which shows the device as it would appear in use to provide secondary intravenous medication to a patient. In this depiction the conical shield 11 has been attached to the intravenous tube 19 by sliding it downward along said tube to cause the outer rounded portions of the slotted opening to deform upwardly to allow said tubing 19 to enter and be secured in hole 16 and the lower cylindrical portion 20 of the device has been lowered over the admixture "Y" 21 and by virtue of an additional slotted hole 22 in said cylindrical section 20 been securely locked in mating engagement with the admixture "Y" 21. The secondary solution needle 23 is shown inserted through the rubber diaphragm 24 of the admixture port 25 and the segment 13 of the conical shield 11 has been raised into locking engagement of the cylindrical depression 15 and the secondary intravenous solution tubing 26. The primary and secondary solutions mix at the confluence of the "Y" 21 and flow into the patient medicating intravenous tubing 27.

In FIG. 3 the device is depicted as having been rotated 90° axially to show with greater clarity the manner in which the segment 13 and the cylindrical depression 15 come into locking engagement and the manner in which the needle protective sheath or cap 28 is retained at hand, yet out of hand, while awaiting the resheathing or recapping operation.

FIG. 4 depicts an alternate embodiment of the present invention in which a plurality of additional solutions may be introduced through a single admixture site. It is similar in many respects to the devices in FIGS. 1, 2 and 3 but differs in that it provides an expanded injection field 29 and comprises a locking spiking needle for insertion into a single needle admixture site. Said spiking needle 30, being surrounded by the cylindrical lower body 32 of the device, is protected from contamination, while the administering individual is protected from an accidental needle strike by virtue of the fact that the needle is enclosed within said cylindrical lower body 32. It is to be noted that this embodiment also comprises the same slotted hole 16 in the conical shield 11 and a similar segment 13 with hinge-points 14 and in this embodiment, a plurality of semi-cylindrical locking depressions 15. It is also provided with a plurality of holes 18 proximate the periphery of the conical shield 11 for the retention of needle protective sheaths or caps.

FIGS. 5 and 6 depict an enhanced detail the slotted hole locks 22 and 33 which are common to both embodiments of the invention.

FIG. 7 depicts, in plan-view, a detail of the manner in which the intravenous tubing 26 is retained within the arcuate (190°) portion 15 of the hinged segment 13.

MODE OF OPERATION OF THE INVENTION

The utilization of the present invention is accomplished by first installing the device on the intravenous admixture site, this is achieved by placing the cylindrical lower body 20 of the device over the vertical portion of the admixture site 25 and applying manual force to bring the two members into complete mating engagement. During the application of this manual force the slotted hole lock 22 will be forced to open allowing the slot to pass over the offset "Y" 21 portion of the admixture site. As the limit of engagement is reached the slot closes effecting positive locking of the two members in mating engagement. The primary intravenous admixture tubing 19 is then pressed into the slotted opening 17 into hole 16 to provide additional mechanical support for the device and removing tension stresses from the admixture site and the connecting tubing. The intravenous admixture protective device is now in place and position to assume its protective function. The secondary intravenous solution container is suspended and its connecting tube and sheathed or capped needle are brought into proximity with the conical shield 11 and the needle sheath is inserted into one of the plurality of sheath retention holes 18 in the conical shield. While holding the needle shank between the fingers of one hand, the administering individual grasps and holds the needle sheath with the fingers of the other hand, simultaneously withdrawing the needle from the sheath and leaving said sheath to repose in the sheath retention hole. The grasp on the sheath is released and transferred to the cylindrical lower body 20 of the device to hold and support the admixture site during the insertion of the secondary solution needle. Following insertion of the admixture needle the peripheral hinged 14 segment 13 is raised and the secondary solution tube 26 is pressed into the cylindrical depression 15 positively and securely locking the tubing and needle into place and virtually eliminating the possibility of accidental removal.

When it is desired to remove the secondary solution needle the reverse of this procedure is followed, inserting the used needle into the sheath prior to bringing the other hand into proximity with the needle until said needle is again safely within its protective sheath. In the event that other hypodermic procedures are performed, the additional sheath retention holes 18 in the shield provide a convenient temporary means and method for safely removing, storing and resheathing needles.

The apparatus and mode of operation of the present invention affords safe, simple and effective means for protecting the health and well-being of health-care professionals who must routinely be in proximity with patient's body fluids and provides an extra measure of safety to the patient by assuring that life-sustaining medication will not be accidentally disconnected.

While there has herein been shown and described the presently preferred form of this invention, it is to be understood that such has been for purposes of illustration only, and that various changes may be made therein within the scope of the appended claims.

What is claimed is:

1. A protective apparatus of the type to be positioned in surrounding relationship with a conventional intravenous admixture port assembly containing an injection port branch, said protective apparatus comprising:
   (a) an elongated cylindrical member of a predetermined length sufficient to extend beyond the injection port branch of said admixture port, said cylinder comprising an internal diameter dimensioned slightly larger than the outer diameter of the injection port branch of said admixture port,
   (b) entrance means comprising an integrally formed opening at the distal end of said cylindrical member, dimensioned to pass over the injection port branch of said admixture port, (c) locking means integrally formed on said cylindrical member adjacent said entrance means to selectively engage or disengage said cylindrical member with or from said admixture port, (d) said locking means comprising a dimensionally reduced slotted opening interposed between said dimensioned opening for the admixture port assembly and the distal end of said cylinder, (e) said slotted opening comprising at the distal portion thereof, relief in the form of rounded corners, to facilitate passage over the admixture port through slight deformation of said dimensionally reduced slotted opening, (f) said cylindrical member comprising at the upper portion thereof an integrally formed conical shield constructed of a durable plastic material, (g) said shield being in the form of a truncated cone, said cone being fixedly attached, at the frustum thereof to the upper end of said cylindrical member in the manner of a funnel, (h) said cone comprising adjacent to the periphery thereof a dimensioned hole, (i) said hole having a narrow slot interposed between it, and communicating with, the outer periphery of said cone, (j) said conical shield having for half the circumference thereof a semi-detached member, said member being integrally formed and attached to said cone by diametrically opposed hinge members which allow upward rotation of said semi-circular semi-detached member to achieve perpendicularity with relation to the base of said cone, (k) said semi-circular semi-detached member having at midpoint thereof, an additional semi-circular portion comprising at least 190° of arc, said portion being open for the remaining 170°, (l) said 190° semi-circular portion being dimensioned to accommodate standard intravenous tubing, (m) said conical shield having within the periphery thereof, at a point proximate the mid-point between the base of said cone and the frustum thereof, at least one dimensioned hole.

2. A protective appliance as in claim 1 wherein said cylindrical portion comprises a substantially hollow interior extending along the length thereof, as positioning means, dimensioned to engage the exterior periphery of an admixture injection site in mating engagement and thereby substantially center the appliance of the injection port thereof.

3. A protective device as in claim 1 wherein said cylindrical portion comprises a dimensioned hole to accommodate the "Y" portion of an admixture device.

4. A protective appliance as claim 1 wherein said cylindrical portion comprises a slot of a dimension less than that of the "Y" portion of an admixture device, said slot being situate between the dimensioned hole and the distal end of said cylindrical portion.

5. The protective appliance of claim 1 wherein the distal end of said slot comprises rounded ends to facilitate the entry of the "Y" portion of the admixture device into the dimensioned slot, which upon slight deformation, opens to allow entry to the dimensioned hole, thereby substantially locking the cylindrical member of the appliance in positive mating engagement with the admixture device.

6. The protective appliance of claim 1 wherein the conical shield is integrally formed on said cylindrical body means in surrounding relation to the opening to encompass and substantially center said appliance on the admixture injection site.

7. The protective appliance of claim 6 wherein said conical shield comprises a plurality of dimensioned holes diametrically arranged within the periphery thereof, said holes being dimensioned to accommodate the protective sheaths of hypodermic injection needles.

8. The protective appliance of claim 7 wherein said conical shield comprises a single dimensioned hole proximate the periphery thereof, said hole being intersected by a narrow slot passing outward radially through the periphery of said shield.

9. The protective appliance of claim 6 wherein said semi-circular semi-detached member comprises a narrow section of the periphery of the conical shield, the conical shield having a slit extending for one-half the circumference of said shield, said narrow section being hinged at diametrically opposed points along the periphery of said conical shield to allow its elevation into perpendicularity with the base of the conical shield int he manner of the "bail" or handle of a water pail.

10. The protective appliance of claim 9 wherein the said narrow, semi-circular section has along the length thereof, one or a plurality of semi-circular depressions, each including an angle of at least 190° the interior of which are dimensioned to correspond with the outside diameter of standard intravenous tubing.

11. The protective appliance of claim 1 wherein the cylindrical member is elongated and comprises a spiking needle at its center, said needle being positioned to penetrate the injection site of an admixture device as the protective apparatus is installed upon said admixture device.

12. The protective appliance as in claim 11 wherein the elongated cylindrical member thereof comprises a protective encirclement of a length greater than the entire length of said spiking needle, thereby preventing contact contamination of said needle and positively preventing inadvertent or accidental skin puncture by said needle.

13. A protective appliance as in claim 11 wherein the injection site or field is enlarged to accommodate a plurality of admixture needles thereby allowing the administration of a plurality of medications through a common injection port.

14. The protective appliance of claim 11 wherein the semi-detached member comprises a plurality of semi-circular portions each comprising an angle of at least 190°, said depressions being dimensioned to accommodate the exterior diameter of standard intravenous tubing providing means to securely retain said tubing thereby preventing the accidental removal of the injection needles from the injection site.

* * * * *